United States Patent
Vu et al.

(10) Patent No.: US 9,186,229 B2
(45) Date of Patent: Nov. 17, 2015

(54) TOOTHBRUSH CHARGING STATION WITH BRUSH STORAGE DEVICE

(75) Inventors: Phong Vu, Schwalbach (DE); Ivo Kunath, Kronberg/Taunus (DE); Martin Haas, Eschborn (DE); Norbert Schaefer, Frankfurt am Main (DE); Alexander Hilscher, Oberursel (DE)

(73) Assignee: Braun GmbH, Kronberg (DE)

( * ) Notice: Subject to any disclaimer, the term of this patent is extended or adjusted under 35 U.S.C. 154(b) by 821 days.

(21) Appl. No.: 13/157,356

(22) Filed: Jun. 10, 2011

(65) Prior Publication Data

US 2011/0315572 A1 Dec. 29, 2011

Related U.S. Application Data

(63) Continuation of application No. PCT/IB2009/055668, filed on Dec. 10, 2009.

(30) Foreign Application Priority Data

Dec. 11, 2008 (EP) ..................................... 08021498

(51) Int. Cl.
| | |
|---|---|
| *B65D 85/20* | (2006.01) |
| *A47K 1/09* | (2006.01) |
| *A47B 81/02* | (2006.01) |
| *A61C 17/00* | (2006.01) |
| *A45D 44/18* | (2006.01) |
| *A61C 19/02* | (2006.01) |
| *A61C 17/22* | (2006.01) |

(52) U.S. Cl.
CPC ............... *A61C 17/00* (2013.01); *A45D 44/18* (2013.01); *A61C 19/02* (2013.01); *A61C 17/224* (2013.01)

(58) Field of Classification Search
CPC ......... A47B 88/20; A47K 1/09; A45D 44/18; A61C 19/02; B65D 81/133
USPC ................... 206/216, 361, 362, 362.1, 362.2; 211/65, 119.009; 320/108, 115
See application file for complete search history.

(56) References Cited

U.S. PATENT DOCUMENTS 1,954,085 A * 4/1934 McMillan ................... 206/362.1
2,713,940 A * 7/1955 Putnam et al. ................ 206/362

(Continued)

FOREIGN PATENT DOCUMENTS

| EP | 0688527 A | 12/1995 |
|---|---|---|
| EP | 1825827 A | 8/2007 |

(Continued)

OTHER PUBLICATIONS

International Search Report for Z8354MQ dated Mar. 11, 2010.

*Primary Examiner* — Chun Cheung
(74) *Attorney, Agent, or Firm* — Alexandra S. Anoff

(57) ABSTRACT

A storage device for tooth cleaning attachments of a tooth cleaning device is provided. The storage device includes a storage body for storing the tooth cleaning attachments. The storage body has a storage base with at least one storage depression for receiving a tooth cleaning attachment in flat-lying alignment.

7 Claims, 6 Drawing Sheets

(56) References Cited

U.S. PATENT DOCUMENTS

| | | | |
|---|---|---|---|
| 3,143,697 A * | 8/1964 | Springer | 320/115 |
| 3,371,260 A * | 2/1968 | Jackson et al. | 320/115 |
| 3,418,552 A * | 12/1968 | Holmes | 320/108 |
| 3,463,994 A | 8/1969 | Spohr | |
| 3,840,795 A * | 10/1974 | Roszyk et al. | 320/108 |
| 4,573,569 A * | 3/1986 | Parker | 206/1.7 |
| D291,268 S | 8/1987 | Stephenson | |
| 5,295,575 A * | 3/1994 | Gonzalez | 206/204 |
| 6,027,081 A | 2/2000 | Rosenberg | |
| 6,053,338 A * | 4/2000 | Avery et al. | 211/65 |
| 8,464,868 B2 * | 6/2013 | Kruger et al. | 206/362.1 |
| 2003/0034315 A1 * | 2/2003 | Tayebi | 211/65 |
| 2009/0127214 A1 | 5/2009 | Kruger et al. | |

FOREIGN PATENT DOCUMENTS

| | | |
|---|---|---|
| JP | 01-129804 A | 5/1989 |
| JP | 05-168529 A | 7/1993 |
| JP | 06-029483 U | 2/1994 |
| JP | 07 255526 A | 10/1995 |
| JP | 2005-143990 A | 6/2005 |
| WO | WO 2008/144875 A | 12/2008 |

* cited by examiner

TOOTHBRUSH CHARGING STATION WITH BRUSH STORAGE DEVICE

CROSS REFERENCE TO RELATED APPLICATION

This application is a continuation of International Application No. PCT/IB2009/055668, filed Dec. 10, 2009, which claims priority to EP 08021498.4, filed Dec. 11, 2008, the substance of which is incorporated herein by reference.

FIELD OF THE INVENTION

The present disclosure relates to a storage device for tooth cleaning attachments. More particularly, the present disclosure relates to a storage device for attachment brushes for a tooth cleaning device, which can be coupled onto or uncoupled from a hand-held part of the tooth cleaning device. The present disclosure also relates to a charging station for a tooth cleaning device including such a storage device.

BACKGROUND OF THE INVENTION

It is frequently the case with electric toothbrushes that one handpiece is shared among different users in a household so that corresponding exchangeable cleaning attachments, for example, attachment brushes, can be placed in a common handpiece and must be held in readiness for the different users. In addition, there are various cleaning and care attachments such as, for example, a dental floss holder for interdental cleaning, polishing elements comprising elastomer elements for removing discolorations from the teeth, tongue cleaners and other cleaning and care attachments for daily oral care which, even when the hand-held part of the tooth cleaning device is only used by one user, result in a plurality of tooth cleaning attachments which must be stored in the proximity of the hand-held part. In order that these additional tools and replacement brushes are not stored at different locations in the bathroom and need to be looked for or become dirty, various storage devices have been proposed directly on the charging part of the hand-held parts of the tooth cleaning devices which are usually operated by rechargeable battery.

For example, U.S. Pat. No. 3,463,994 discloses a toothbrush charging station with an integrated storage box for the replacement brushes which together with the hand-held part is protected from contamination by a joint cover. In this case, the bottom of the storage box comprises a plurality of blind holes into which the attachment brushes can be inserted with their stem ends, which are adapted per se so that they fit exactly to the stem cross-section to avoid any wobbling around of the upright toothbrushes. However, due to liquid or toothpaste residue running down, contamination can occur which adversely affects the insertion and withdrawal of the replacement brushes. In addition, when the cover is open, liquid or moisture dripping down from the replacement brushes can run down laterally from the storage body or what is even worse, run into the hand-held part opening of the charging station in which the hand-held part is inserted for purposes of charging. A disadvantage with these previously known storage devices is additionally the drying of the used replacement brushes. Sufficient circulation of air does not take place due to the ventilation openings provided in the upper side of the cover. In addition, dirt and dust penetrates into the storage container via the said ventilation openings in the upper side of the cover.

Further, known are storage systems in which the replacement brushes are suspended perpendicularly in the air or are stored suspended in a type of rotatable carousel. By this means the problem of blind-hole receptacles becoming blocked by toothpaste residue can certainly be ameliorated, but liquid dripping down leads to unsightly contamination of the wash basin. Further, storage devices have already been proposed which include a mandrel on which the replacement brushes or cleaning attachments are placed so that the replacement brushes or cleaning attachments stand vertically on the charging part ready for gripping. However, systems having such a placement mandrel also have significant disadvantages. On the one hand, the brush must be threaded precisely onto the mandrel for placement which, however, requires a high accuracy and fine motor skills on the part of the user and is frequently difficult for elderly users. On the other hand, mandrel and replacement brush or cleaning attachment must fit exactly into one another, thus resulting in high requirements for the accuracy of the mandrels during manufacture. If the clearances are too tight, the replacement brush jams during placement. If contaminant deposits of toothpaste form on the mandrel, the placement and removal process no longer runs smoothly. In order to avoid removing the charging part during withdrawal, the charging part must be held firmly with the second hand. On the other hand, the replacement brushes or cleaning attachments wobble to and fro and do not always stand vertically if the clearance between mandrel and replacement brush is configured to be too large. Regardless of this, cleaning of the mandrels and the adjacent region around the mandrels is difficult since there is no flat surface which can be completely wiped and very narrow radii are obtained at the transition between mandrel and base surface.

It is therefore desirable to provide an improved charging station of the said type and an improved storage device which obviate the shortcomings of the prior art and hold the tooth cleaning attachments in readiness in an intuitively ascertainable manner which allows easy handling by the user and is at the same time, easy to clean and has favourable production costs.

SUMMARY OF THE INVENTION

In once embodiment, a storage device for tooth cleaning attachments of a tooth cleaning device is disclosed. The storage device includes a storage body for storing the tooth cleaning attachments. The storage body has a storage base with at least one storage depression for receiving a tooth cleaning attachment in flat-lying alignment.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

DETAILED DESCRIPTION OF THE INVENTION

Figure 1:
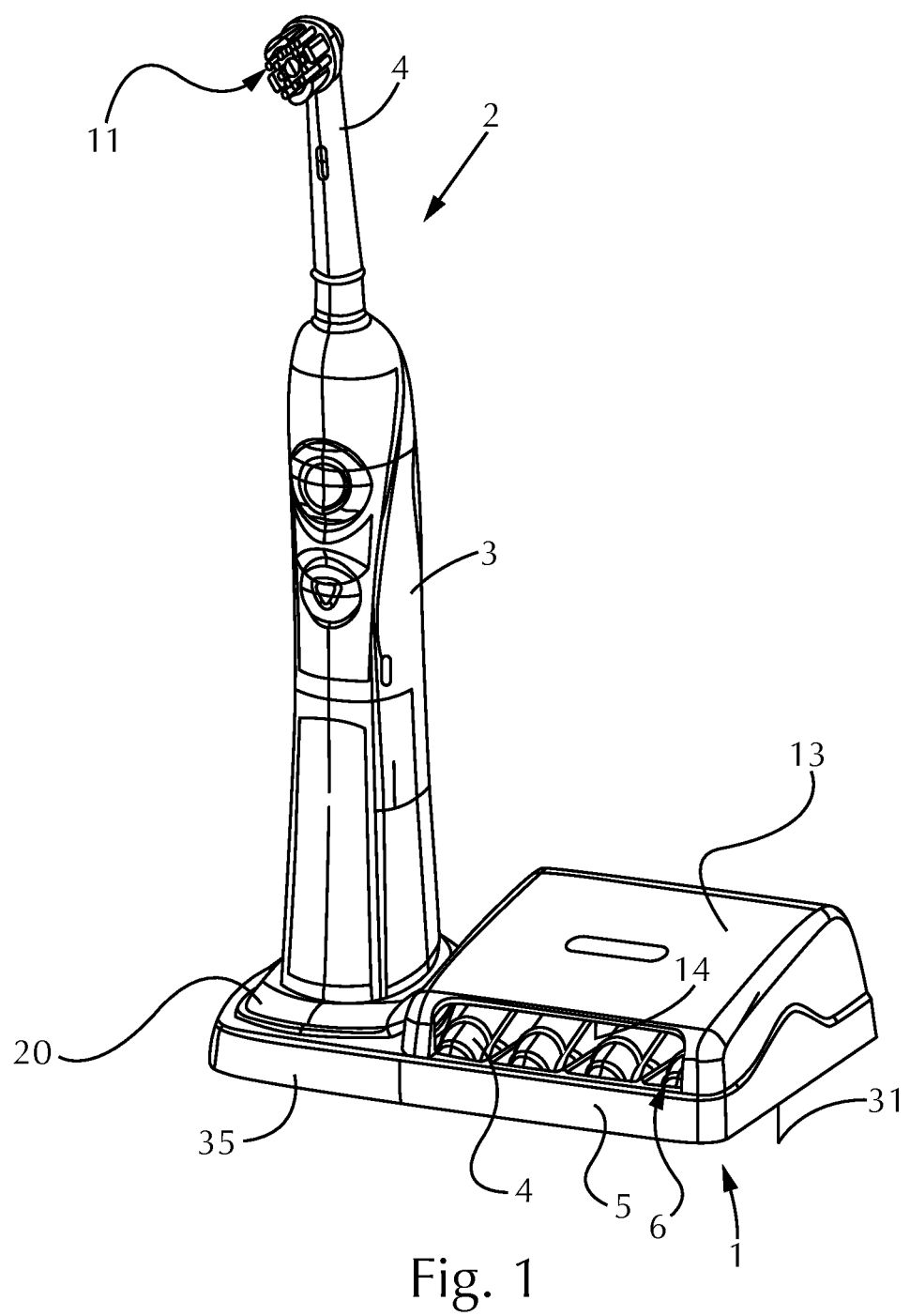
FIG. 1 shows a perspective overall view of an electric toothbrush on a charging station having a storage device for the attachment brushes of the toothbrush connected thereto, in accordance with one embodiment.

According to the present disclosure, tooth cleaning attachments are no longer stored upright on the charging station but rather, in flat-lying alignment. The tooth cleaning attachments thereby no longer extend upright with their longitudinal axis, which is defined by the longitudinal extent of the stem in the case of attachment brushes, but flat-lying, i.e. substantially horizontally or slightly inclined hereto.

According to one embodiment, the storage body of the storage device has a storage base with at least one storage depression for receiving a tooth cleaning attachment in flat-lying alignment. As a result, any tight clamping and corresponding clamping means or positive retaining means such as mandrels and the like on the storage body can be dispensed with. Since no clamping means need to be provided, the storage device is flexible and suitable for different cleaning attachments having different diameters or lengths. Due to the flat-lying storage in conjunction with the storage depressions, a stable positioning of the tooth cleaning attachments is nevertheless obtained. At the same time, the handling for the user is very much simpler since accurate threading-on is unnecessary. The user can simply and, so to speak, blindly set down and remove his cleaning attachment again to place it on the hand-held part. In addition, the storage base is substantially easier to clean than a retaining device with mandrels.

In a further embodiment, the storage base can be configured in the manner of a storage shell and have a plurality of storage depressions for a plurality of tooth cleaning attachments. In order to avoid contamination of the washbasin by draining liquid or toothpaste residue from the tooth cleaning attachments, the storage base can in particular form a drain-free collecting shell having a closed bottom, which descends from its edges towards the center and/or is delimited at the edges by a bead-shaped edge web so that moisture or liquid dripping from the tooth cleaning attachments stored on the storage base collects, and dripping onto the washbasin is prevented.

In another embodiment, the storage base can have a relief-like curved storage surface which is divided by a plurality of storage depressions which can be formed in the storage surface. As a result, the storage body acquires an overall closed and at least to some extent, smooth and/or continuous surface which is easy to wipe and clean. In addition, the storage body can be manufactured with only a few machining steps. For example, the storage body can be injection-molded from plastic without blind-hole receptacles or the like being incorporated in separate processing steps such as drilling or milling.

In one embodiment, the area of the storage depressions and/or adjoining the storage depressions, the storage base has sink-shaped working-head recesses in which the working heads of the tooth cleaning attachments can be accommodated in a downwardly hanging manner. A stable and orderly alignment of the stored tooth cleaning attachments is obtained as a result of this type of storage because, due to the weight of the working heads, these always tend to point downwards. As such, the attachment brushes always turn downwards, regardless of how they are stored. For example, if the attachment brushes are laid simply flat, pointing upwards on the storage surface, they always tilt in an undefined manner to the right or the left. In one embodiment, the working heads of the tooth cleaning attachments stored on the storage base are released downwards so that they can be aligned such that they hang downwards. The tooth cleaning attachments lie rotatably in the storage depressions which in each case define an axis of rotation parallel to the stem for the tooth cleaning attachments. In one embodiment, the working-head recess in the storage base has sufficiently large dimensions that simple insertion is ensured and the working heads can self-align by twisting even when inserted obliquely.

In particular, the depth of the working-head recesses is dimensioned in such a manner that in the storage position of the tooth cleaning attachment, the working head can be accommodated in a suspended manner free from contact in the working-head recess and does not touch its base. In order to allow the self-alignment of the tooth cleaning attachments, the storage base of the storage body is configured to be free from clamping means, i.e. the tooth cleaning attachments are not clamped in the storage depressions. On the contrary, the tooth cleaning attachments are held in the storage depressions due to their weight.

In one embodiment, the storage depressions have gutter-shaped stem receiving sections, whose curvature is matched in shape to the stem diameter of the tooth cleaning attachments in such a manner that the tooth cleaning attachments centre themselves in the storage depressions due to their own weight and come to rest in a precisely fitting manner but without being clamped therein. The storage depressions may have a radius of curvature which is somewhat larger than the stem diameter of the tooth cleaning attachments. The storage depressions can have supporting sections, spaced apart from one another, for the stem of the respective cleaning attachment, between which the cleaning attachment has no contact with the storage base.

In one embodiment, the stem-receiving sections of the storage depressions can be separated from the aforesaid working-head recesses by a step-shaped shoulder in the storage base, wherein in the area of the shoulder, half-shell-shaped supporting means are provided for the neck section of the tooth cleaning attachment so that the working head of the respective tooth cleaning attachment projects in a freely overhanging manner beyond the shoulder and nevertheless comes to rest stably. Due to a sufficient height difference of the storage base beyond the shoulder, it is achieved that the working head, in particular the bristle array of an attachment brush, can be stored in a freely suspended manner on the storage base.

In order to more efficiently remove liquid bound in the bristle array or the working head after teeth cleaning and rinsing, and to allow faster drying of the working head, the storage base and/or the respective storage depression is provided with a slope so that the tooth cleaning attachments come to rest with their longitudinal axis slightly inclined with respect to the horizontal. The slope of the storage depressions and/or the storage base can overall be configured with an angle between about 1° to about 45° with respect to the horizontal, wherein the slope can be configured in such a manner that the tooth cleaning attachments come to rest at an angle of from about 5° to about 25° with respect to the horizontal.

The slope can be oriented in such a manner that the working head of the respective tooth cleaning attachment comes to rest higher than the end of the stem facing away from the working head. As a result, moisture bound to the working head flows downwards, which assists the drying of the working head and in particular a bristle array which is important for hygiene reasons. In addition, the tooth cleaning attachments can be gripped better as a result and these can be viewed better especially when the charging station or the storage device is situated relatively high on a bathroom shelf and/or the respective user is relatively short.

In order to protect tooth cleaning attachments lying on the storage base from contamination with dust and dirt, in one embodiment, a cover is provided which can be placed on the storage surface. In order to ensure easy handling, a hinged cover can be provided which, in one embodiment, can be pivoted about a horizontal hinge axis which can extend along the side of the storage base facing the working heads of the stored tooth cleaning attachments or the working-head recesses provided for this purpose.

In one embodiment, the cover can be configured to be hood-shaped and have a closed upper side which prevents any penetration of falling dust into the storage container. In order to achieve good drying of the tooth cleaning attachments and allow escape of moisture, in another embodiment, at least two ventilation openings are provided in the cover and/or in the storage base to achieve circulation of air in the interior or through the interior of the storage container. The ventilation openings can be arranged and configured in such a manner that a chimney effect is achieved between the ventilation openings which considerably improves the air circulation and therefore the drying of the tooth cleaning attachments. For example, at least two ventilation openings disposed at different heights can be provided, the two ventilation openings being configured in the cover such that of these, one is formed at the lowest point of the cover and the other is formed at the highest point of the cover.

The configuration of the cover making it possible to achieve such a chimney effects is based on the reasoning that moist air has a lower specific weight than dry air and therefore rises. In order to ensure that the working heads of the tooth cleaning attachments are swept by the air draught effected by the chimney effect, in a further embodiment, one ventilation opening is provided below the storage position of the working heads and a corresponding further ventilation opening is provided above the said working-head position.

In order, on the other hand, not to impair the dust protection function, however, the upper ventilation opening is not formed in the upper side of the hood-shaped cover but on the upper edge of one of the side flanks of the cover, wherein in particular a ventilation slit can be provided in the transition zone between the upper side of the cover and the side flank of the cover. In another embodiment, the ventilation opening disposed on the opposite side of the cover is disposed at the lower edge of the side flank of the cover.

In order to assist the chimney effect, the upper side of the cover is configured to be inclined, the slope ascending towards the cover side in which the upper ventilation opening is formed. In another embodiment, the inclined upper side of the cover has a continuous and in particular, continuously ascending profile so that no accumulation effects can formed which could impair the chimney effect.

In order to allow a sufficient chimney effect, in another embodiment, the ventilation openings overall have a cross-sectional area of at least about 1000 mm². In principle in this case, the overall cross-sectional area can be divided in different ways among the plurality of ventilation openings. In a further embodiment, the at least two ventilation openings each account for about 25% of the total area of all the ventilation openings. In particular, two ventilation openings provided on opposite sides can be provided, whose individual cross-sectional area in each case accounts for at least about one third of the total cross-sectional area of all the ventilation openings.

In order to prevent moisture collecting on the inclined storage base from dripping onto the washbasin located thereunder, the storage base in configured in a shell-shape and/or enclosed by a bead-shaped edge web which, at one end adjoins the storage depressions for the tooth cleaning attachments and at the same time can form a stop forming a positioning and/or alignment means for the tooth cleaning attachments at which these can stand in particular with their stem end.

This edge web can be configured to be lower in height that the diameter of the stem sections of the tooth cleaning attachments so that the tooth cleaning attachments project slightly with their stem end over the edge web of the storage base. This makes it easier to grip the tooth cleaning attachments. In addition, identifiability of the respective tooth cleaning attachments can hereby be improved. In order to individually code different tooth cleaning attachments, colored markings, for example, in the form of a small ring may be provided, which the user places at the front on his or her attachment brush or on his or her cleaning attachment. In the placement solutions with a mandrel specified initially, this ring frequently can no longer be seen which also applies to the initially specified prior art with blind-hole receptacles. As a result, gripping the wrong attachments can occur or several brushes must be inspected until the right one has been found. In contrast to this, in the case of flat storage in particular in conjunction with the only limited height of the lateral edge webs of the storage base, the coding rings are readily visible. In this context, the height of the edge web and/or the stop at the end of the storage depression is less than about 75%, in another embodiment, less than 50% of the stem diameter of the tooth cleaning attachments to be stored and/or of the diameter of the storage depressions defined by the radius of curvature. Handling is thus made easier and the risk of confusion reduced.

In order to provide storage of the tooth cleaning attachments immediately adjacent to and/or in the proximity of the hand-held part of the tooth cleaning device, in one embodiment, the storage body of the storage device can be connected to the charging station for charging the hand-held part. The storage body can be formed integrally in one piece on the housing of the charging station so that storage of the attachments is provided permanently at the charging station.

In one embodiment, a modular structure of charging station and storage device is provided so that the tooth cleaning attachments can be stored directly at the charging station or separately from this as desired. For example, the storage body can have detachable connecting means for detachable fastening to the charging station so that, for example, a fixed connection between charging station and storage device can be made for use at home. In another embodiment, for use when travelling, the charging station can be carried alone and stored separately from the storage device. The modular structure brings with it particular advantages independently of the horizontal storage of the tooth cleaning attachments. Thus, for example, only the small, very compact charging part can be taken along for shorter journeys whilst the relatively bulky storage device in comparison can be left at home. Conversely, only the storage device can be taken when one knows that a corresponding hand-held part is available at the destination such as, for example, a holiday apartment.

In one embodiment, the detachable connecting means between the storage body and the charging station can be differently configured. For example, screwing and/or clamping of the storage body to the charging station can be provided. In a further embodiment, the detachable connecting means comprise locking means for locking the storage body on the charging station. In order to provide a sufficiently fixed connection between charging station and storage body despite the detachability of the connection, in one embodiment, the storage body has a charging station receiving opening which is matched in shape to the charging station and/or which can be placed over the housing of the charging station and hereby connected in a positive. The charging station opening can be annularly closed so that the charging station is completely enclosed when the storage body is placed thereon and the edge of the charging station opening so to speak nestles in a precisely fitting manner against the outer contour of the charging station.

In order to be able to guide out the mains cable provided at the charging station, in one embodiment, the storage body, in particular a circumferential wall of the annularly close charging station opening can have a cable penetration recess which can be configured in the form a U-shaped through recess, open towards the bottom. Depending on the configuration of the charging station and/or the mains cable connection, the cable penetration recess can have connecting means integrated on the storage body, in the form of locking means for detachable connection or locking of the storage body on the charging station.

Turning to the figures, FIG. 1 shows an electric toothbrush as a tooth cleaning device 2 comprising a hand-held part 3 and tooth cleaning attachments 4 in the form of attachment brushes which can be detachably placed on the hand-held part 3, and which can be driven by an electrical drive in the hand-held part 3 in a manner known. In this case, the tooth cleaning attachments 4 can comprise a tubular stem 23 and a working head 24 connected thereto, which in the case of attachment brushes is configured as a brush head. However, as has already been explained initially, other tooth, gum, tongue and/or oral cavity treatment and/or care tools also come into consideration such as, for example, interdental cleaners, tongue cleaners and the like. The hand-held part 3 includes, in a manner not shown in detail, an energy storage device in the form of a rechargeable battery which can be charged by placing the rear face of the hand-held part 3 on the charging station 20.

Figure 6:
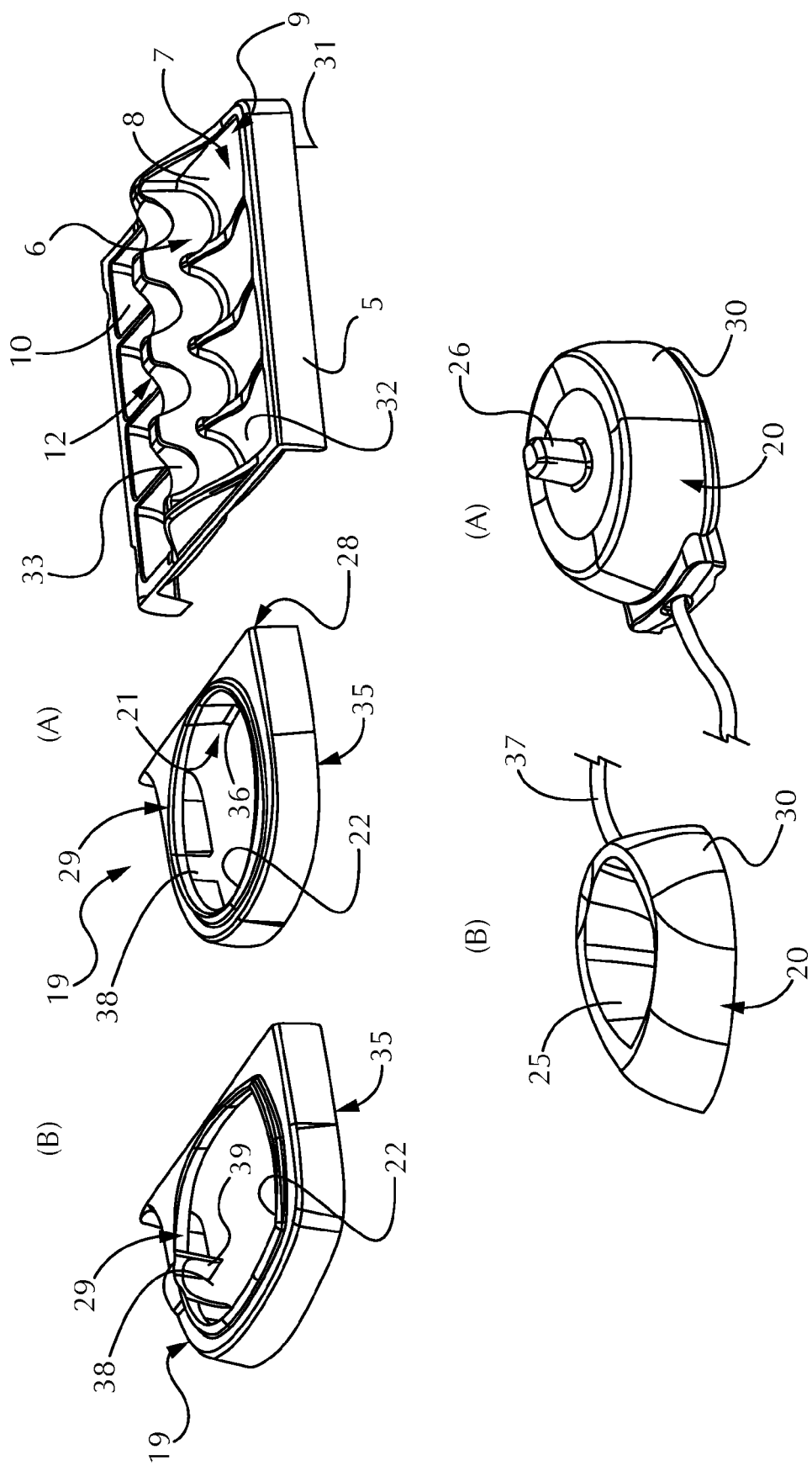
FIG. 6 shows a perspective schematic view of the storage body of the storage device according to a further embodiment of the invention whereby the storage device possesses a modular structure and different holders for different charging stations can be connected to the storage body, wherein according to FIG. 6 the actual storage body and the charging station holders connectable thereto are shown in an exploded view.

The charging station 20 includes a hand-held part receptacle 25 which is matched in shape to the hand-held part 3, in particular to its rear face, and which can be configured differently depending on the hand-held part. As shown in FIG. 6 in variant (A), the hand-held part receptacle 25 can include a protruding mandrel 26 which engages in a front recess on the hand-held part 3. Alternatively or additionally, as shown in design option (B) in FIG. 6, the hand-held part receptacle 25 can include a blind-hole-shaped recess into which the hand-held part 3 can be inserted. The electrical contact for the purpose of charging the hand-held part 3 can be configured in various ways in a known manner.

Figure 2:
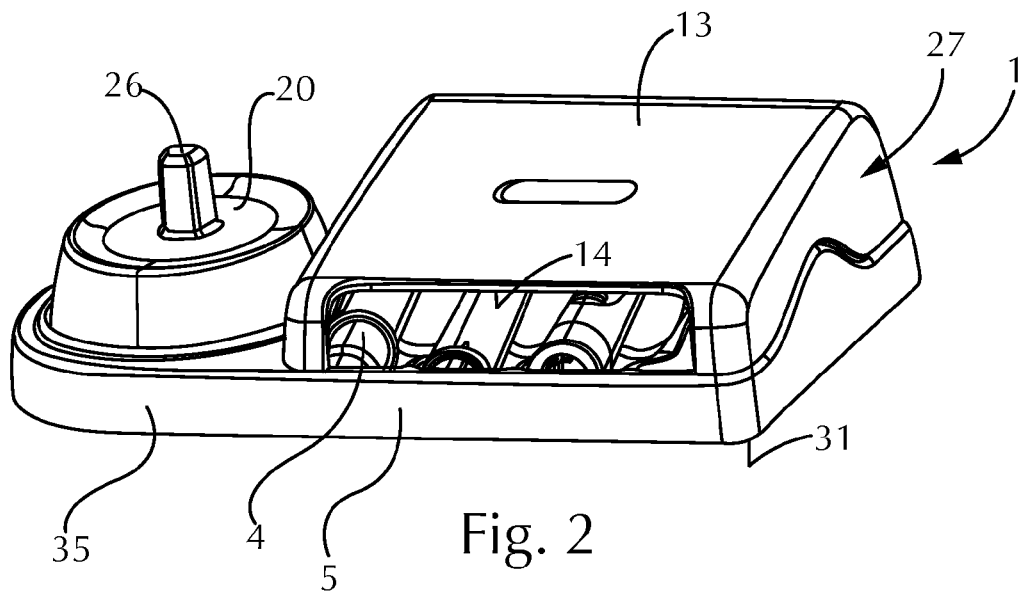
FIG. 2 shows a perspective view of the storage device for the attachment brushes and the charging station connected thereon, wherein the storage device is shown with the cover closed.
Figure 3:
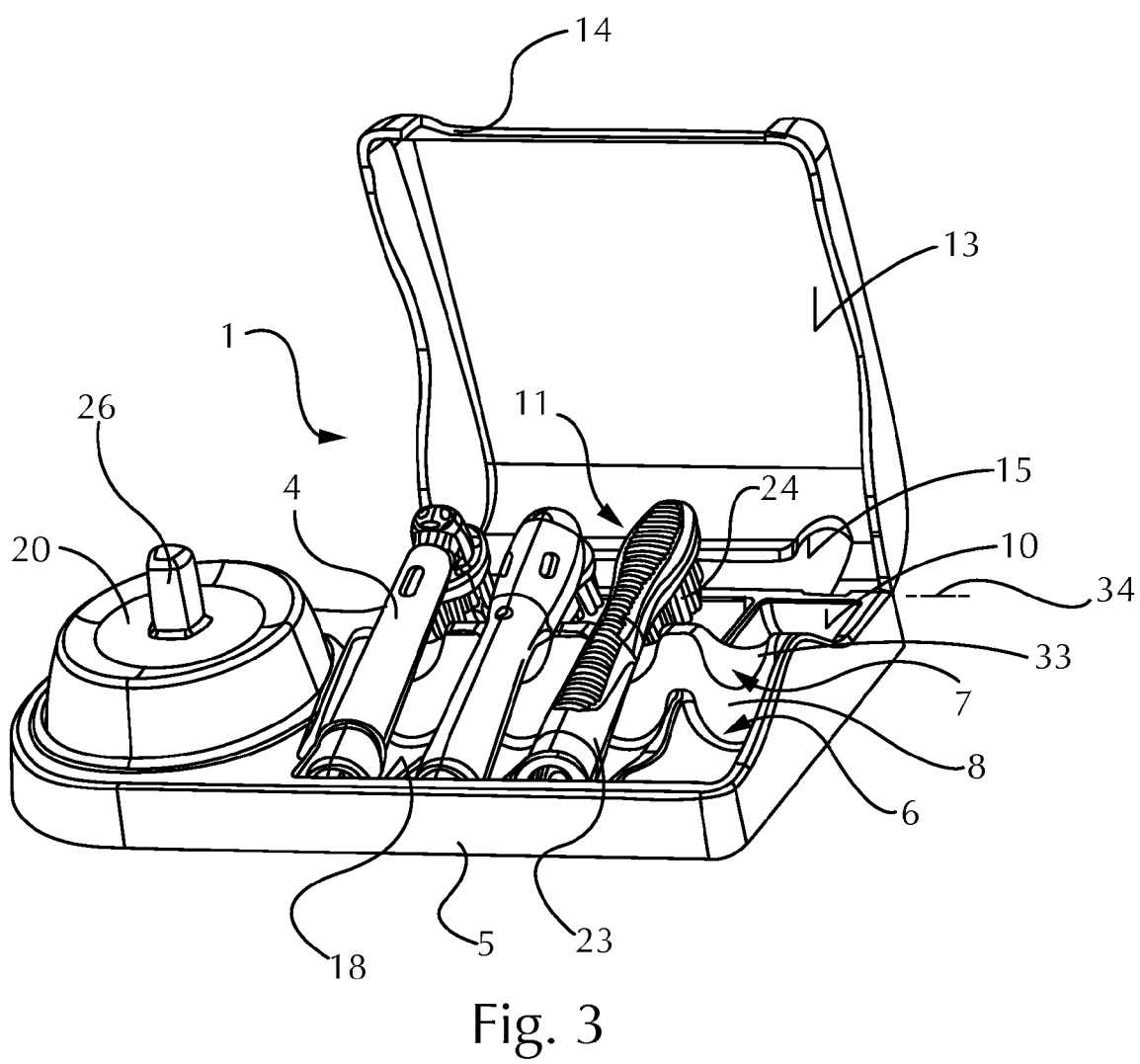
FIG. 3 shows a perspective view of the storage device adjacent to the charging station similar to FIG. 2, wherein the cover of the storage device is shown open and three attachment brushes are stored on the storage base of the storage device.

In the embodiment shown in FIGS. 2 and 3, the storage device 1 can be connected to the charging station 20, said storage device including in the figures a closable storage container 27 in the manner of a casket into which a plurality of tooth cleaning attachments 4 can be placed.

Figure 7:
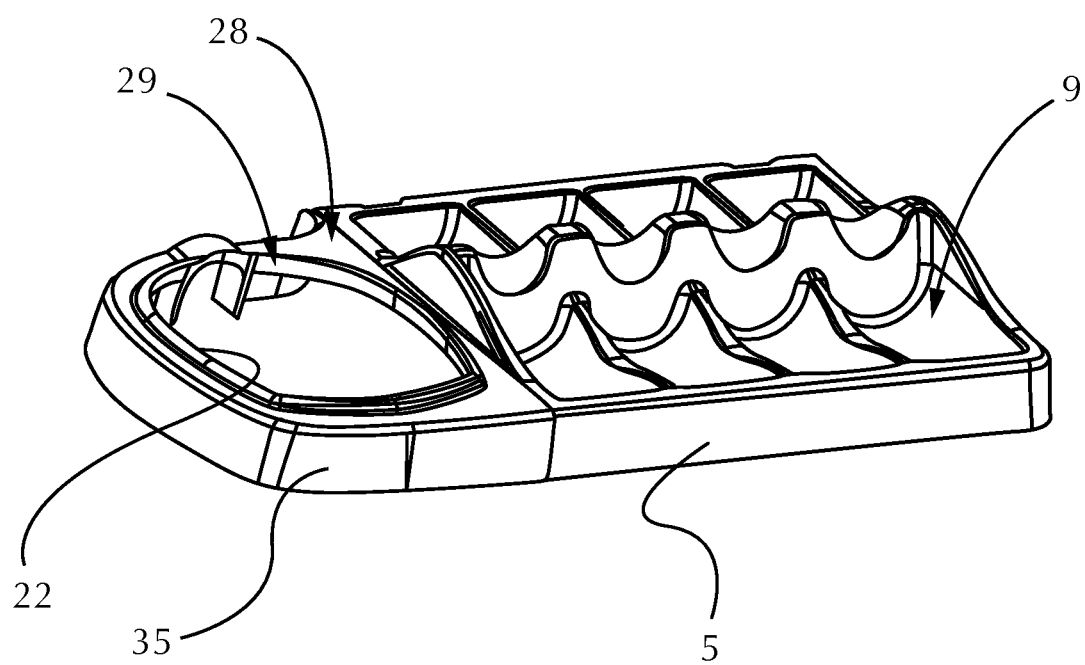
FIG. 7 shows a perspective view of the storage body from FIG. 6 with the charging station holder connected thereto according to option (B) from FIG. 6.

In the embodiment depicted in FIGS. 2 and 3, the storage container 27 includes an integrally formed connecting means 28 in the form of a charging station holder 29 which can be fastened to the housing 30 of the charging station 20. Instead of the integrally formed connecting means 28, the storage device 1 can also have a modular structure with separately configured and advantageously exchangeable connecting means 28, as shown in FIGS. 6 and 7 and as will be explained in further detail below.

The storage device 1 includes a storage body 5 which forms a lower part of the storage container 27 and has a flat contact zone 31 by which means it can be placed on a washbasin, a bathroom shelf or the like. The contact zone 31 can include contact elements, for example, in the form of small feet made of a soft material, in order to achieve low-noise and cushioning standing on the base. In order to avoid slipping on a smooth base, contact elements can be provided, for example, in the form of feet, made of an elastomer or rubber, wherein these contact elements can be moulded on or mounted separately.

For this purpose, the storage body 5 possesses a flat, plate-like configuration and can be placed with a flat side on the base. In particular, the said storage body can include a relief-like curved storage base 6 on which a plurality of tooth cleaning attachments 4 can be placed in flat-lying alignment.

Figure 5:
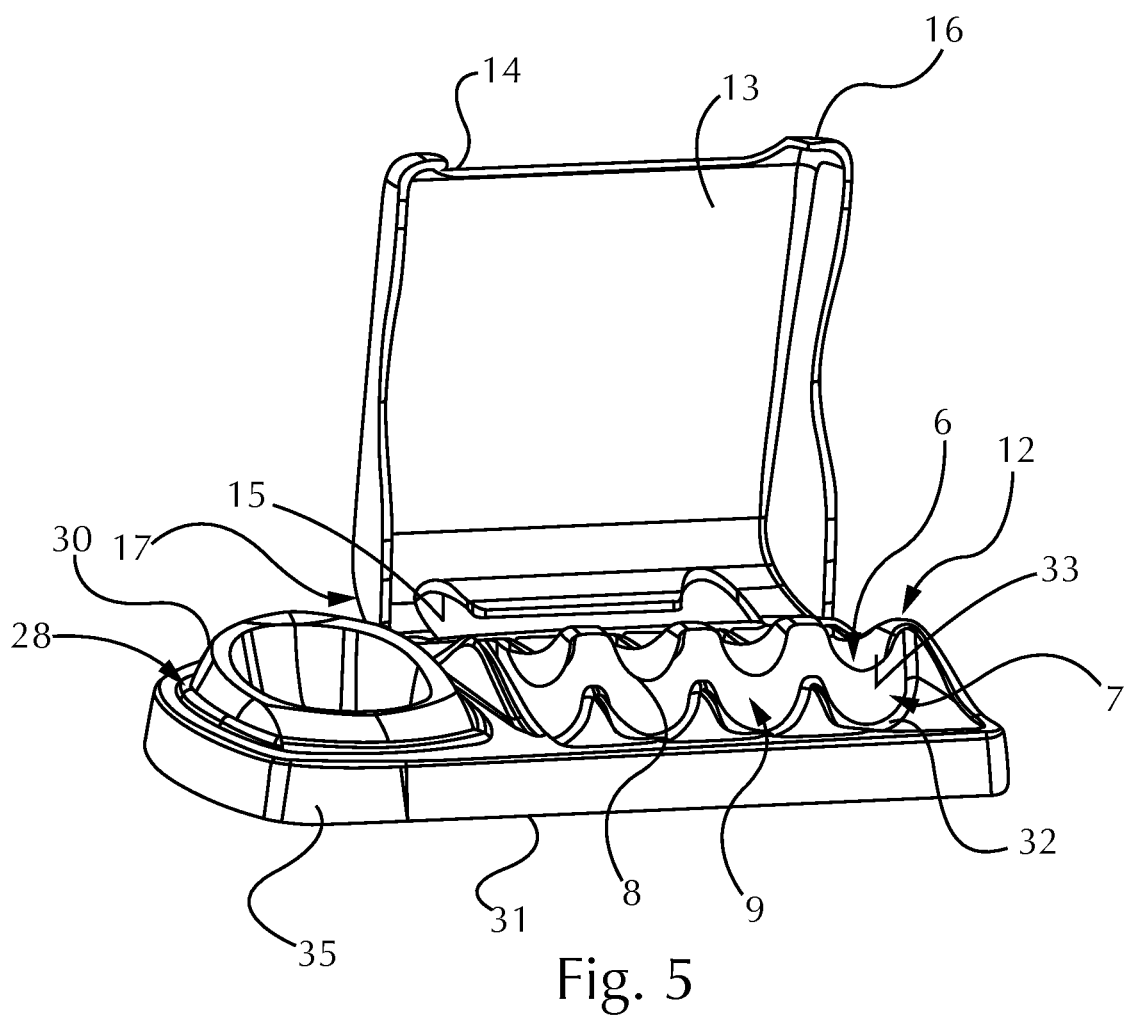
FIG. 5 shows a perspective view of the storage device from FIG. 4, wherein the cover is shown in the open position and the storage device is shown without attachment brushes to be stored.

As shown in FIGS. 3 and 5, a plurality of, in the embodiment shown four, storage depressions 7 are incorporated in the storage base 6, which in the form of half-shell-shaped and/or gutter-shaped depressions are matched in shape to the contour of the tooth cleaning attachments 4 and in particular their tubular stems 23. In the embodiment shown, the storage depressions 7 are configured in such a manner that the tooth cleaning attachments 4 do not rest thereon over the total length of their stems 23 but are supported at points or at two support positions. For this purpose, the storage depressions 7 comprise two respectively half-shell-shaped support sections 32 and 33 which are aligned flush with one another, between which the contour is lowered so that the stems 23 of the tooth cleaning attachments 4 lie freely between the said support sections 32 and 33 and have no contact with the storage base 6. In this embodiment, the support sections 32 and 33 are arranged in such a manner that the tooth cleaning attachments 4 rest thereon with an end section of the stems 23 and with a neck section shortly before the working head 24, see FIG. 3.

The two support sections 32 and 33 thereby together form respectively one stem storage section 9 of a respective storage depression 7 in which a respective tooth cleaning attachment 4 with its tubular stem can be placed so that the respective stem 23 rests in a known manner on an end section and on a neck section but between these two sections, comes to rest freely and without contact with the storage base 6.

Following the stem storage section 9, the respective storage depression 7 then has a section for receiving a working head 24 of the respective tooth cleaning attachment, wherein the stem receiving section 9 and the adjoining section for receiving the working head are arranged linearly one behind the other, at least when viewed in plan view, see FIG. 3.

In one embodiment, in the area of the working heads 24 of the tooth cleaning attachments 4, the storage base 6 includes respectively one working-head recess 10, which forms a depression in the storage base 6 and is configured to be sufficiently large and deep so that the working heads 24, which in the case of tooth cleaning attachments 4 in the form of attachment brushes, form their bristle arrays 11, can be accommodated so that they hang freely downwards without the working heads 24 standing on the storage base 6.

In the embodiment shown, in the area of the storage depressions 7, the storage base 6 includes a staircase-shaped shoulder 12 in the area whereof the storage base 6 shows a difference in height. Towards the aforesaid working-head recesses 10, the storage base 6 drops downwards so that the working heads 24 of the stored tooth cleaning attachments 4 project freely protruding from the respective support section 32, see FIG. 3. In this embodiment, the storage depressions 7 are arranged parallel and adjacent to one another so that the stored tooth cleaning attachments 4 can be stored in parallel alignment adjacent to one another.

In order to achieve better draining of residual moisture at the tooth cleaning attachments 4, the storage depressions 7 are, or the storage base 6 is, slightly inclined at an acute angle to the contact zone 31 of the storage body 5 and in one embodiment, at an angle of from about 5° to about 25°. The slope of the storage depressions 7 is hereby achieved by an arrangement of the aforesaid support sections 32 and 33 at different heights. In particular, the support section 33 facing the respective working head 24 in this case can be arranged slightly higher than the support section 33 provided for the stem end so that the tooth cleaning attachments 4 lie with their working heads 24 slightly elevated, see FIG. 3.

Figure 8:
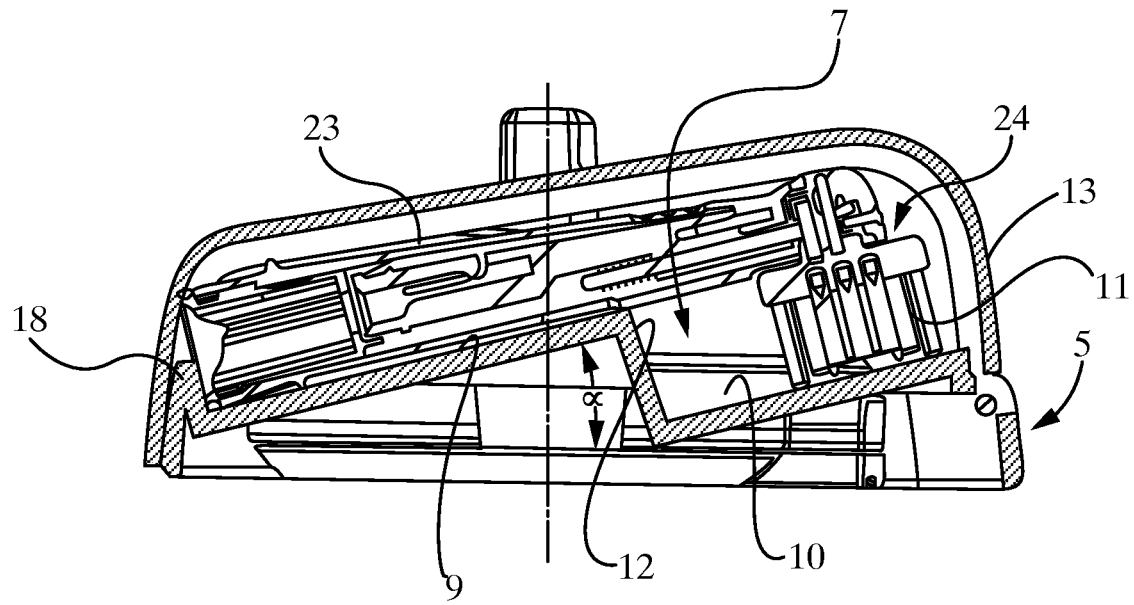
FIG. 8: shows a section through one of the step-shaped contoured storage depressions of the storage body with a working-head recess for the suspended, downwardly released accommodation of a toothbrush head.

As FIG. 8 shows, the stem receiving section 9 of a respective storage depression 7 can also be configured as continuous, i.e. instead of the separate support sections 32 and 33 shown in FIG. 3, a continuous, gutter-shaped stem storage depression is provided, see FIG. 8. In the embodiment according to FIG. 8, the stem storage section 9 is also configured as ascending towards one side, wherein the angle with respect to the horizontal can be between about 5° and about 25°. An angle of inclination α of about 14° is provided in the embodiment in FIG. 8. In this embodiment, the stem storage section 9 can be configured to be ascending towards the working-head recess 10 so that the working head 24 comes to lie higher than the end section of the stem with which the tooth cleaning attachment 4 is placed on the relevant hand-held part.

As FIG. 8 further shows, the working head recess 10 of the storage depression 7 drops downwards with respect to the aforesaid stem storage section 9 due to a staircase-shaped shoulder 12 so that the bristle array 11 of the working head 24 can hang downwards, whereby the bristle array 11 can optionally stand slightly on the base of the working-head recess 10 or can be left free with respect to the base without standing thereon, as shown in FIG. 8.

The storage base 6 is circumferentially bordered by an edge web 18 which is configured to be slightly elevated compared with the storage surface 8 of the storage base 6. With the aid of this edge web 18 the storage base 6 forms a collecting shell which prevents residual moisture from running off from the tooth cleaning attachments 4 onto a washbasin or a bathroom shelf.

At least in the area of the storage depressions 7 on which the tooth cleaning attachments 4 come to lie with their stem ends, the height of the aforesaid edge web 18 is smaller than the diameter of the stems 23 of the tooth cleaning attachments 4, see FIG. 3 or FIG. 8. In one embodiment, the height of the edge web 18 in the area is less than about 75%, and in another embodiment less than about 50% of the height of the stem diameter. It is possible to more easily see and identify the colored rings frequently slid onto the ends of the stems for individual coding of the tooth cleaning attachments 4, in particular if the storage device 1 is standing in an elevated location.

Figure 4:
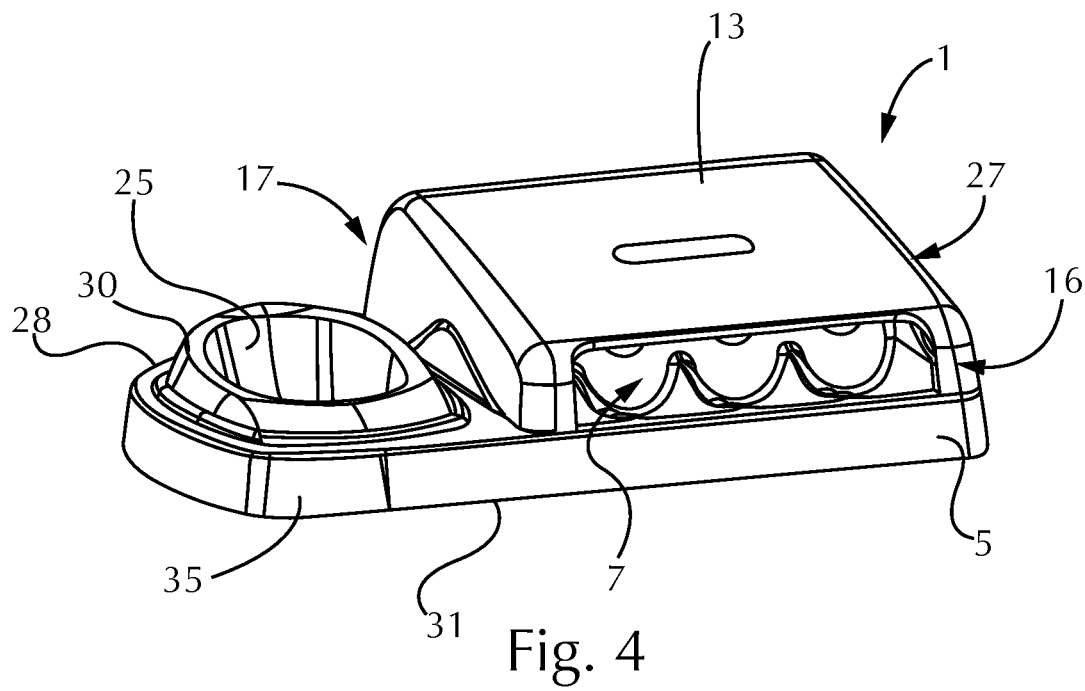
FIG. 4 shows a perspective of the storage device adjacent to the charging station from a slightly modified perspective compared with FIG. 2, wherein the storage device is shown with the cover closed.

As FIGS. 4 and 5 show, the storage body 5 forms a casket-like lower part which can be closed by means of a hood-shaped cover 13. In the embodiment shown, a hinged cover 13 can be provided, which can be opened and shut about a horizontal pivot axis 34 along the side of the storage body 5 on which the working heads 24 of the tooth cleaning attachments 4 come to rest. In this case, the cover 13 covers the entire storage base 6 and sits on the edge web 18 surrounding the storage base 6, see FIG. 4.

In order to achieve sufficient ventilation and as a result, drying of the stored tooth cleaning attachments 4 despite the cover 13, two slit-shaped ventilation openings 14 and 15 can be provided in the side flanks of the cover 13 on opposite sides, which openings extend at the front and back or at the stem ends and the working heads 24, see FIG. 3.

The arrangement and configuration of the ventilation openings 14 and 15 as well as the configuration of the cover 13 overall is made in such a manner that a chimney effect is established between the two ventilation openings 14 and 15. In one embodiment, the rear ventilation opening 15 at the working heads 24 extends at a greater height than the front ventilation opening 14 at the ends of the stems 23. In addition, the upper side of the cover 13 is configured to be inclined and specifically in such a manner that it ascends continuously towards the rear ventilation opening 15. In one embodiment, the slope or inclination of the upper side of the cover 13 can be in the range of from about 5° to about 25°.

The upper side of the cover 13 itself can be configured without openings and closed to protect the stored tooth cleaning attachments 4 from falling dust. In another embodiment, the cover 13 can be made of a transparent plastic material since it can thereby be visually identified when the cover 13 is closed whether and how many and which working heads 24 are located in the storage body 5. The aforesaid ventilation openings 14 and 15 can be provided in the side flanks of the cover 13, wherein they extend there as far as into the transition zone towards the upper side, see FIGS. 2 and 3.

In order to assist the aforesaid chimney effect, only two side flanks 16 and 17 of the cover 13 are provided with ventilation openings 14 and 15 whereas the other two side flanks of the overall rectangular cover 13 are configured to be closed, see FIGS. 2 and 3. In order that the storage container 27 of the storage device 1 can be connected to the charging station 20, the storage body 5 comprises connecting means 28 provided laterally at one end, including a laterally protruding retaining part 35 with a central charging station receiving opening 22. The retaining part 35 continuously continues the contact zone 31 of the storage body 5.

The charging station receiving opening 22 can be matched in shape to the outer contour of the housing of the charging station 20 so that it nestles around the housing of the charging station 20 in a precisely fitting manner when the retaining part 35 is pushed over the charging station 20.

In order to achieve a fixed connection between the retaining part 35 and the charging station 20, locking means 21 can be provided in the area of the charging station receiving opening 22, which locking means can, for example, include locking hooks 36 projecting radially from the circumference of the charging station receiving opening 22, which can engage with complementarily shaped locking edges on the housing of the charging station 20. As a result of the detachable connection between the storage body 5 and the charging station 20, the storage device 1 can optionally be used together with the charging station 20 or separately from this. In particular, it is possible to take merely the slim charging station 20 when travelling if, for example, there is not sufficient room in a suitcase.

In order to be able to lead out a mains cable 37 of the charging station 20, the circumferential wall of the charging station receiving opening 22 includes a cable penetration recess 38 which, as shown in the depicted embodiment, can be configured in the form a U-shaped through recess open towards the bottom so that the storage device 1 with the retaining part 35 can easily be placed onto the charging station 20 from above and placed via the mains cable 37. Depending on the configuration of the mains cable 37 or its connection to the charging station 20, retaining means, for example, in the form of locking projections 39 can be incorporated in the cable penetration recess 38, see FIG. 6, embodiment (B) therein. The mains cable 37 or a mains cable connection can be held positively with such locking means.

Whereas FIGS. 2 to 5 show an embodiment whereby the retaining part 35 for the charging station 20 is formed integrally in one piece on the storage device 1, it can also be possible to configure the retaining part 35 separately and connect it detachably to the storage body 5, as shown in FIGS. 6 and 7. Due to such a further modularly configured structure of the storage device 1, it is in particular possible to arrange and fasten different retaining parts 35 on the storage body 5, which are suitable for different charging stations 20. FIG. 6 shows two such differently configured retaining parts 35 in embodiments (A) and (B) which have differently configured charging station receiving openings 22 which are matched in shape to the respective embodiments (A) and (B) of the charging station 20.

In one embodiment, the connection between the retaining part 35 and the storage body 5 can in principle be differently configured. A positive detachable connection in the form of a locking connection may also be provided.

Figure 9:
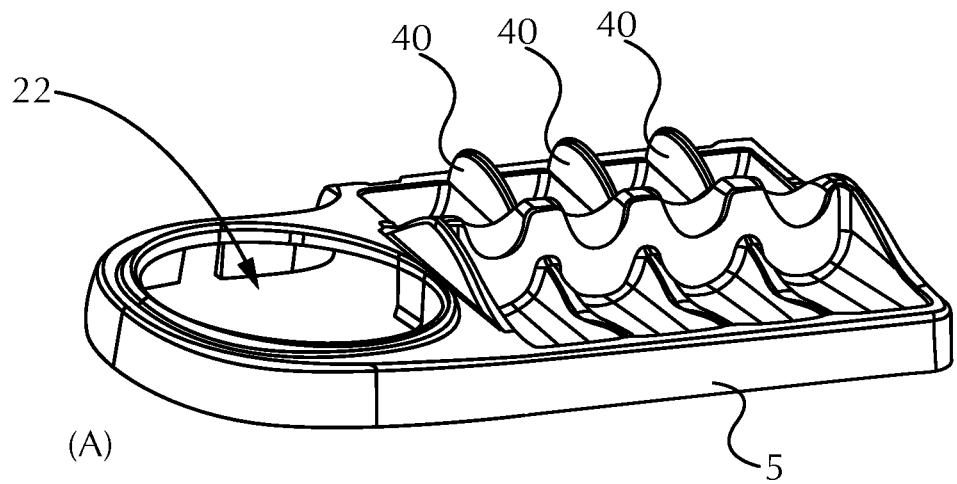
FIG. 9 shows a perspective view of the storage body similarly to FIG. 7 but with raised partition walls.

FIG. 9 shows a perspective view of the storage body similar to FIG. 7 but with raised dividing walls 40 which prevent mutual contact of the working heads 24 laid in the storage depression 7, in particular the bristle arrays 11, thus preventing any contamination of a material and/or bacterial nature. In this exemplary embodiment, the storage body 5 is configured in one piece with the charging station receiving opening 22, preferably as a plastic injection molded part.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A storage system for tooth cleaning attachments of a tooth cleaning device comprising:
a storage body wherein the storage body comprises a storage base for storing a plurality of tooth cleaning attachments and a charging station receiving opening; and
a charging station for charging a tooth cleaning device the charging station including a housing wherein the charging station is configured for a hand-held part of the tooth cleaning device such that the hand-held part has a substantially vertical alignment when charging;
wherein the storage base comprises a relief-like curved storage surface which is divided by a plurality of storage depressions and in which the plurality of storage depressions have gutter-shaped stem storage sections having a curvature matched in shape to a stem diameter of the tooth cleaning attachments and wherein the storage depressions are arranged parallel and adjacent to one another;
the storage base further comprises a plurality of sink-shaped working-head recesses for receiving a plurality of tooth cleaning attachments in a downwardly hanging manner and a flat-lying alignment wherein the working-head recesses are adapted for receiving a working-head of the tooth cleaning attachment having a depth sufficient to accommodate the working-head in a suspended manner and without standing on the storage base;
and wherein the charging station receiving opening is matched in shape to the charging station to allow the storage body to be releasably attached to the housing of the charging station.

2. The storage system according to claim 1, wherein the storage base forms a storage shell.

3. The storage system according to claim 1, wherein the storage base has a slope with an angle of from about 1° to about 45° with respect to the horizontal, by which means the tooth cleaning attachments can be placed at an inclination to the horizontal on the storage base.

4. The storage system according to claim 3, wherein the slope towards the working-head recess is configured to be ascending.

5. The storage system according to claim 1, wherein the storage base is configured to be free of clamping means.

6. The storage system according to claim 1, wherein the storage body has detachable connecting means for fastening the storage body to a charging station for the hand-held part of the tooth cleaning device.

7. The storage system according to claim 6, wherein the detachable connecting means includes locking means for locking the storage body on the charging station.

* * * * *